United States Patent
Alber

(10) Patent No.: US 6,879,659 B2
(45) Date of Patent: Apr. 12, 2005

(54) RADIOTHERAPEUTIC APPARATUS

(75) Inventor: Markus Alber, Tübingen (DE)

(73) Assignee: Elekta AB, Stockholm (SE)

( * ) Notice: Subject to any disclaimer, the term of this patent is extended or adjusted under 35 U.S.C. 154(b) by 102 days.

(21) Appl. No.: 10/450,369

(22) PCT Filed: Dec. 13, 2001

(86) PCT No.: PCT/EP01/14684

§ 371 (c)(1),
(2), (4) Date: Jun. 12, 2003

(87) PCT Pub. No.: WO02/49044

PCT Pub. Date: Jun. 20, 2002

(65) Prior Publication Data

US 2004/0066892 A1 Apr. 8, 2004

(30) Foreign Application Priority Data

Dec. 13, 2000 (GB) .............................................. 0030358

(51) Int. Cl.⁷ ................................................ A61N 5/10
(52) U.S. Cl. ......................................... 378/65; 378/64
(58) Field of Search ........................... 378/64, 65, 152, 378/153

(56) References Cited

U.S. PATENT DOCUMENTS 6,473,490 B1 * 10/2002 Siochi .......................... 378/65
6,560,311 B1 * 5/2003 Shepard et al. ................ 378/65

* cited by examiner

Primary Examiner—David V. Bruce
Assistant Examiner—Hoon Song
(74) Attorney, Agent, or Firm—Bromberg & Sunstein LLP

(57) ABSTRACT

An optimization method for a fluence pattern to be provided via a radiotherapeutic apparatus comprising a multi-leaf collimator comprises an iteration of a progressive solution (such as a gradient approach) of the fluence profile, at least some iterations including a weighted penalty function which varies between solutions favored by the collimator design and solutions not so favored, later iterations including the penalty function at a greater weight. Thus, the penalty function represents locally preferred solutions derived from the constraints of the multi-leaf collimator (MLC). As the iteration progresses, the greater weight assigned to the penalty function drives the method towards a solution which is possible given the MLC constraints. However, the lesser weight attached in the early stages of the iteration allows the method to settle towards a genuinely preferred solution. Overall, therefore, the method migrates towards a theoretically ideal solution and then diverts to a nearby practically possible solution. In this way, a solution is obtained which can be put into practice but is close to a theoretically ideal solution, ie a solution that would be preferred in the absence of MLC constraints. It is preferred that the penalty function is calculated over a part of the fluence profile in the region of the then location of the iteration solution. The method can be embodied in a suitable computer program, which can be stored on a data carrier. An apparatus can comprising a storage means in which the program is located and a processing means for running the program.

14 Claims, 3 Drawing Sheets

RADIOTHERAPEUTIC APPARATUS

FIELD OF THE INVENTION

The present invention relates to a radiotherapeutic apparatus.

BACKGROUND ART

The clinical realisation of intensity modulated radiotherapy (IMRT) requires sophisticated technology and honed treatment procedures if high standards of quality assurance and time efficiency are to be met. The expense rises dramatically for highly irregular fluence distributions if multi-leaf collimators (MLC) are used. It has been shown in references 1 and 2 that the optimisation problem of IMRT allows sufficient latitude to fine-tune the resulting fluence distributions to increase clinical utility.

Although these methods facilitate the translation of fluence distributions into the motion patterns of the MLC, they do in general not ensure the most efficient application or even feasibility of the fluence distributions as delivered by the optimisation algorithm. Ideally, the limitations of the application device are already taken into account during the optimisation of the fluence distributions. This is of particular importance for application techniques where the beam is switched off while the leafs are moving to the positions which define the outline of the next field segment. In this case, the fluence distribution is piecewise constant with a finite, usually small number of discontinuities.

The necessity of piecewise constant fluences also arises in IMAT with the additional constraint that fluence steps may not be displaced relative to the beam between two positions of the arc by more than a certain distance dictated by the finite leaf velocity. A sliding window dMLC technique requires piecewise linear fluence profile with the additional condition that the increase or decrease between two vertices (which are the DICOM control points) is equal for all leaf rows, only the position of these vertices may vary between rows.

SUMMARY OF THE INVENTION

The present invention seeks to provide a radiotherapeutic apparatus which is able to derive an MLC movement schedule from (for example) a desired IMRT treatment with an improved optimisation. The invention is applicable to IMRT techniques, and also to dMLC, close-in dMLC, IMAT and static "step and shoot" techniques. The preferred embodiment will be described with reference to IMRT but this does not detract from the generality of the invention.

The present invention therefore provides an optimisation method for a fluence pattern to be provided via a radiotherapeutic apparatus comprising a multi-leaf collimator, the method comprising an iteration of a progressive solution of the fluence profile, at least some iterations including a weighted penalty function which varies between solutions favoured by the collimator design and solutions not so favoured, later iterations including the penalty function at a greater weight.

Thus, the penalty function represents locally preferred solutions derived from the constraints of the multi-leaf collimator (MLC). Typically, it will have a large number of minima. As the iteration progresses, the greater weight assigned to the penalty function drives the method towards a solution which is possible given the MLC constraints. However, the lesser weight attached in the early stages of the iteration allows the method to settle towards a genuinely preferred solution. Overall, therefore, the method migrates towards a theoretically ideal solution and then diverts to a nearby practically possible solution. In this way, a solution is obtained which can be put into practice but is close to a theoretically ideal solution, ie a solution that would be preferred in the absence of MLC contraints.

A suitable progressive iterative solution is a gradient based approach. In such methods, the local gradient of the multi-dimensional surface representing the function to be minimised (for example) is ascertained and the next iterative step is made in a direction corresponding to a downward gradient. Over successive iterations, a minima is eventually reached.

It is preferred that the penalty function is calculated over a part of the fluence profile in the region of the then location of the iterating solution. Ideally it is centred there. This minimises time spent on unnecessary calculation. It is however preferable for the penalty function to be recalculated during the iteration as the set of feasible solutions varies as the optimisation proceeds and hence the penalty function varies.

Through this invention, the processing time for arriving at a solution can be reduced, and solutions which are closer to optimal or simpler can be arrived at. Thus, the usage time of processing equipment can be reduced for each treatment, allowing the equipment to be used more efficiently. Also, simpler or more optimal solutions will often involve shorter treatment times, giving evident benefits for the patient and allowing more patients to benefit from IMRT treatment.

It is preferred that the method is embodied in a suitable computer program. Accordingly the present invention also relates to that program, to the program stored on a data carrier, and to an apparatus comprising a storage means in which the program is located and a processing means for running the program.

BRIEF DESCRIPTION OF THE DRAWINGS

An embodiment of the present invention will now be described and explained, by way of example, with reference to the accompanying figures, in which.

An adjustment of the angle of the field would result in an unimodal fluence distribution.

Figure 6:
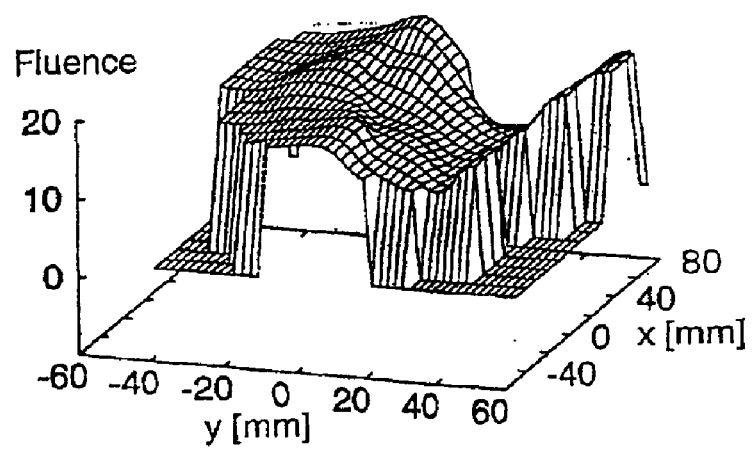
FIG. 6 shows the fluence distribution of the posterior oblique field. The rectum corresponds to the shielded region.
Figure 7:
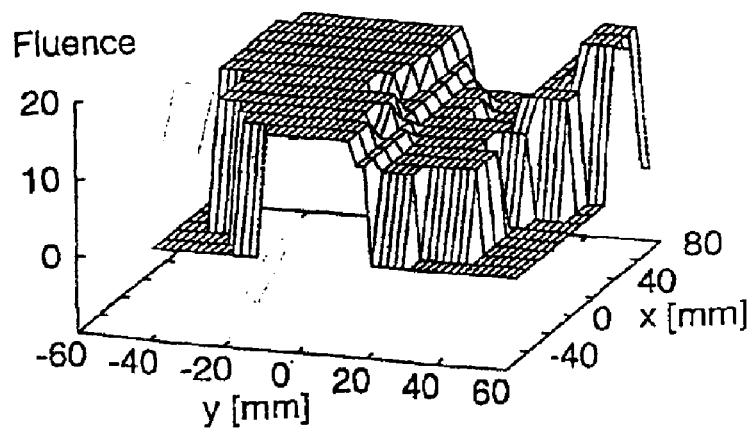

FIG. 7 shows the same field as FIG. 6, with MLC constraints applied. The field has eight segments.

DETAILED DESCRIPTION OF THE EMBODIMENT

The setting of the optimisation problem is as follows. Let the fluence distribution $\phi(x,y)$ of a given field be composed of fluence elements termed rays $R_{ij}$, i=1, . . . ,n, j=1, . . . ,m with fluence $\phi_{ij}$ on a regular grid [ia, (i+1)a[x[jb, (j+1)b[ for some real distances a, b. The positions of a pair of leafs at times $t_1$, $t_2$ . . . can be described by coordinates with respect to the grid defined by the fluence elements. The total fluence of a ray is the ray fluence $\phi_{ij}$ multiplied by the fluence weight $\phi_{ij}$.

The fluence distribution is translated by an operator P into a piecewise constant function with clusters of fluence elements of the same weight. These clusters result in a set of leaf coordinates and total fluences for each time $t_k$ such that this treatment plan is applicable with the given equipment. Such a pair of leaf coordinates and fluence is termed segment. This translation may be subject to complicated constraints related to the engineering details of the MLC. The hypothetic translator P groups the fluence elements such that the fluence distribution consists of the minimum number of stacked segments of maximum size.

Figure 1:
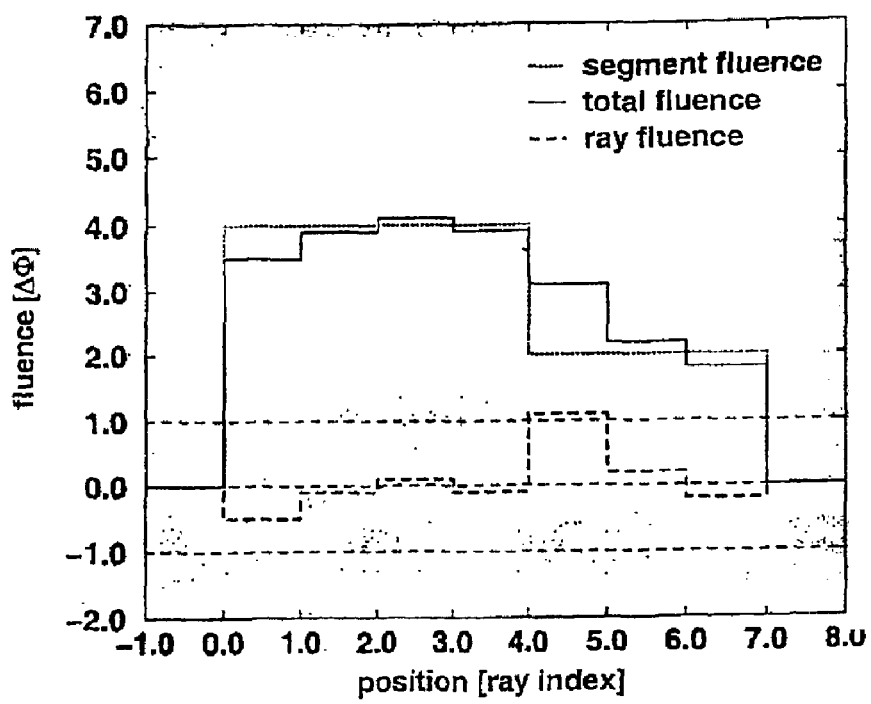
FIG. 1 shows an example of the decomposition of the total fluence into segment fluence and ray fluence. Two segments are present, S1 from ray index 4 to 6, and S2 from index 0 to 3. After a minimisation of $\hat{f}$ the rays may attain intermediate fluence weight values. The operator P would set the weight of all rays to 0 apart from ray 4 which is above the fluence increment threshold $\Delta\phi$. This ray would constitute a new segment with fluence weight $\psi=\phi 4+\psi 1$ in the next run.

If a number of fluence elements is exposed during the time interval $[t_k, t_{k+1}]$ while the beam is on, this set of rays is called the segment $S_k$ with total fluence $\psi_k$, see FIG. 1. To allow for an unambiguous correlation between segments and rays, we denote with $S_{ij}$ the smallest segment which contains the ray $r_{ij}$. Likewise, $\psi_{ij}$ denotes the total fluence of the profile which passes through the area delineated by the segment $S_{ij}$. Notice that the fluence of these mathematical segments is not equivalent to the physical fluence passing through the field as delineated by the collimators.

We assume that the optimum fluence distribution can be obtained by minimising an objective function $f(\phi)$ with the property that if there exists one $\phi_{ij}<0$ then $f(\phi)=\infty$ to avoid negative fluence contributions. We assume further that f is a twice continuously differentiable function and does not possess local minima so that the minimum can be found with a fast gradient based algorithm.

There are several ways how the translation operator P can be used directly in conjunction with the optimisation algorithm to deliver an applicable fluence distribution (references 3 and 4). One way is to apply P to the optimum solution $\phi^*$ a posteriori. While P may be constructed such that it does not overly deform the fluence distribution, this procedure does not grant any control over the dose distribution. It cannot be prevented that in some cases $f(P\phi^*)>>f(\phi^*)$.

Another way would be to feed $P\phi^*$ back into the optimisation and apply P regularly at particular iterations of the optimisation algorithm. This can cause erratic behaviour of the optimisation algorithm due to two effects. Firstly, the target set $_{Aly^*}\overset{\Rightarrow\mathfrak{R}}{\mathcal{P}}\subset{} _{Aly^*}\overset{\Rightarrow\mathfrak{R}}{\mathcal{F}}$ of the operator P is non-convex. If we assume that this is the set of all piecewise constant fluence distributions with at most n fluence levels, then a convex combination of two elements can have up to 2n fluence levels, i.e. would not be an element of this set. As a consequence, the objective function will attain multiple local minima on $_{Aly^*}\overset{\Rightarrow\mathfrak{R}}{\mathcal{P}}\subset{} _{Aly^*}\mathcal{F}$. Secondly, the operator P is non-contracting, i.e. fluence distributions whose distance is small (e.g. as measured by the Euclidean norm) can be mapped onto fluence distributions which have a greater distance. This can cause an algorithm using gradient information to oscillate rather than converge.

To obtain a stable and consistent method of incorporating the MLC related constraints, two problems have to be solved. The parameter space over which f is minimised has to be convex, and the translation operator has to be contracting. This is achieved with the following modifications.

1. After each application of the operator P, the parameter space for the next iterations is composed of all rays $R_{ij}$ and all segments $S_k$, i.e. in the following iterations, the fluences of both segments and fluence elements are altered to minimise f. The barrier against negative fluences applies to the total local fluence, i.e. the sum of $\phi_{ij}+\psi_{ij}$. With this alteration, the parameter space is convex, yet the fluence distribution is no longer unambiguously composed of ray fluences.
2. To provide for an unambiguous representation of the fluence distribution, a penalty term is introduced for all rays $R_{ij}$ which centers the fluence around 0

$$g_{ij}=\phi^2_{ij} \qquad (1)$$

Figure 2:
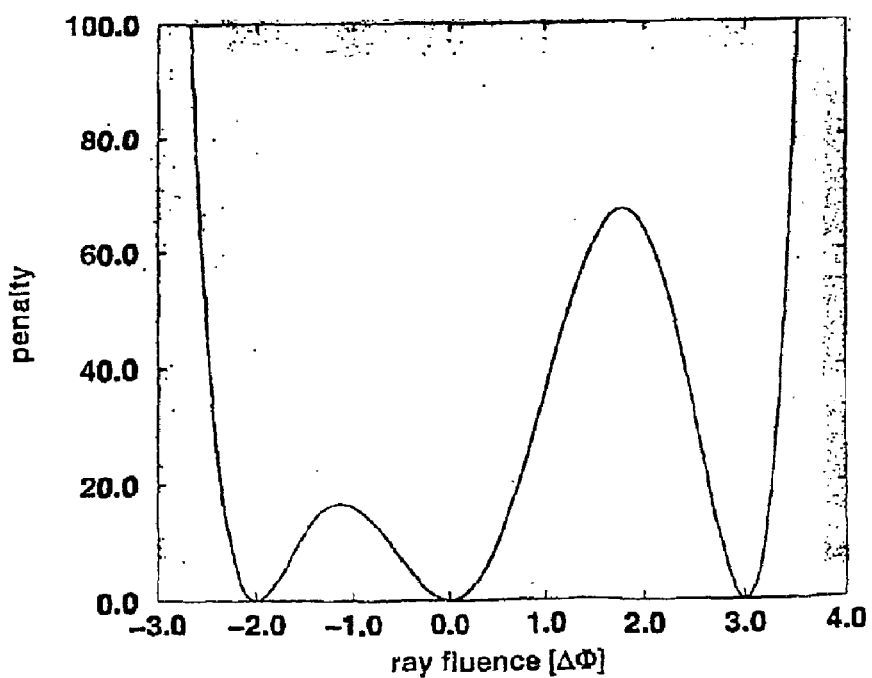
FIG. 2 shows the penalty function of a ray which is a neighbour to two segments, one with fluence increment $-2\Delta\phi$ and one with increment $3\Delta\phi$.

Furthermore, for each neighbouring segment $S_{i'j'}\neq S_{ij}$, i'=i±1, j'=j±1, $g_{ij}$ is multiplied with an additional term $(\phi_{ij}+\psi_{ij}-\psi_{i'j'})^2$, so that $g_{ij}$ is a polynomial of $\phi_{ij}$ with a quadratic minimum at 0 and at each fluence increment to neighbouring segments, see FIG. 2. The sum $g(\phi)$ over all $g_{ij}$ is added to f by means of a penalty multiplier $\lambda$ to yield $\hat{f}$ $$\hat{f}(\phi_{ij}+\psi_{ij})=f(\phi_{ij}+\psi_k)+\lambda(\phi_{ij}) \qquad (2)$$

where we stress the fact that the $\psi_k$ are not considered as variables of g and are included into the optimisation only by means of f. Finding the feasible fluence which minimises f then becomes a two-tier problem. In an inner loop $\hat{f}$ is minimised, in an outer loop the operator P is applied to the result and the multiplier increased. With this arrangement, at high values of $\lambda$ the ray fluences $\phi_{ij}$ are forced to attain values such that the total fluence for ray $R_{ij}$ is either $\psi_{ij}$ or any of the neighbouring fluences $\psi_{i\pm1,j\pm1}$. At low values of $\lambda$ the ray fluences may attain intermediate values. which show their tendency to smooth the edges of the segmented fluence distribution. Thus, the parameter $\lambda$ can be seen as an inverse temperature: at high temperatures the 'spins' $\phi_{ij}$ may flip between 'states' $\psi_{ij}$, $\psi_{i\pm1,j\pm1}$; at low temperatures the spins 'freeze out' in either state representing the 'ground state'. During the course of the optimisation $\lambda$ is increased to reduce the 'temperature' of the fluence distribution. The role of the operator P is to mediate the transitions between states.
3. There is no translation operator for this problem which is generally contracting, but with the multistable penalty introduced above it is possible to condition the fluence distribution such that for this restricted problem a dedicated contracting translation operator can be devised. After the algorithm has converged for a given enlarged parameter space and a given penalty λ, the ray fluences contain information how the current segmenting may be improved. This incremental amendment of the segments prevents oscillation of the optimisation algorithm if the translation operator is fine-tuned to the problem. This can be achieved by a threshold Δφ for the minimum fluence increment between the segment and its surrounding segments; if the increment is below the threshold, the segment is concatenated with its neighbour. Likewise, new segments can only be created if the resulting fluence increment is above the threshold. The criteria according to which new segments are created or existing segments are altered may vary with the cost in terms of treatment time or monitor units incurred by these changes.

Since the translation operator can alter, create and destroy segments, it cannot be generally non-contracting. However, it is contracting for all fluence distributions with ray fluences smaller than Δφ. Since all rays lying above the threshold are grouped into new segments if feasible, eventually the operator will always act on a fluence distribution for which it is contracting. This process is assisted, but not caused by the multistable penalty. The safe convergence was obtained at the cost of additional iterations. The number of segments depends on the threshold Δφ.

The algorithm was described for the application of intensity modulated fields with a static MLC fields, a so-called step and shoot technique. The same fields may be applied while the beam is on leading to a dynamic close-in technique if the segments are arranged accordingly. Since the number of peaks in the fluence distribution can be controlled by the translation operator, it is often possible to derive unimodal fields (with a single peak) for which a dynamic close-in technique is the most efficient both in terms of monitor units and treatment time. Even for multimodal fluence distributions, a series of dynamic close-ins and leaf movements without irradiation may be favourable over other possibilities. For this general case the algorithm has to be slightly modified.

Let $j_l$ be the position of the left leaf of pair i at time $t_k$ and $j_{l+n}$ be the position at time $t_{k+1}$. The right leaf is at a position $j_r > j_{l+n}$ at both times. Let d(R) respectively d(S) be the dose at unit fluence from ray R respectively segment S. If the irradiation is interrupted during leaf travel, the segment dose consists of the sum of the rays $$d(S_k) = \sum_{i=0}^{n-1} d(R_{i,j+1})$$

and segment dose $$d(S_{k+1}) = \sum_{i=0}^{m-n-1} d(R_{i,j+n+i}).$$

In case the irradiation is not interrupted, let the segment dose be composed of $$d(S_k) = \sum_{i=0}^{n-1} (n-i)/n d(R_{i,j+i})$$

and segment dose $$d(S_{k+1}) = \sum_{i=0}^{n-1} i/n d(R_{i,j+i}) + \sum_{i=0}^{m-n-1} d(R_{i,j+n+i}).$$

The linear change of fluence between segment $S_k$ and $S_{k+1}$ corresponds to constant leaf velocity during time $[t_k, t_{k+1}]$.

Results

The output of the algorithm are leaf positions and monitor units per MLC field, thus no translation errors can occur. The number of segments depends highly on the number of fields, the complexity of the treatment plan and the fluence increment threshold Δφ.

Figure 3:
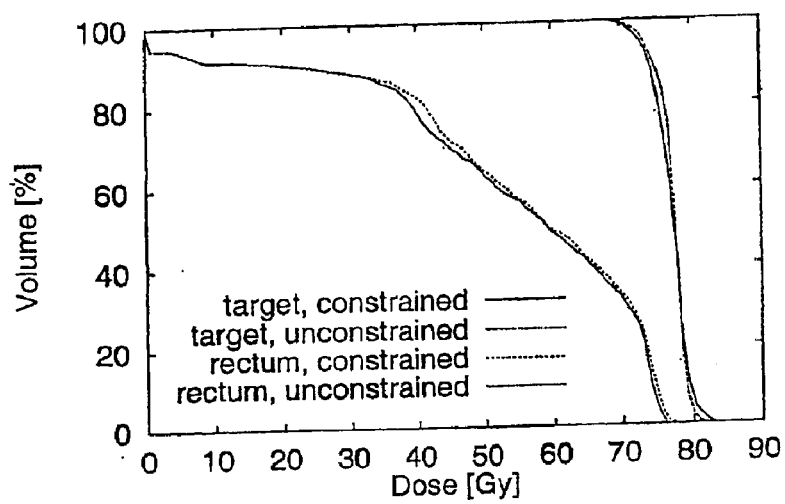
FIG. 3 shows the DVHs of the rectum and the PTV for the example case shows that there is no significant change in the dose distribution. The constrained target dose is slightly less homogeneous.
Figure 4:
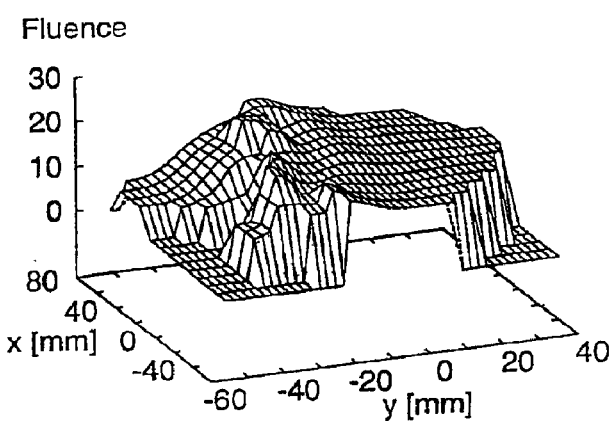
FIG. 4 shows the fluence distribution of the anterior oblique field without MLC constraints. The rectum corresponds to the shielded area to the left. The field size is defined at isocentre distance, the fluence is given in arbitrary units.
Figure 5:
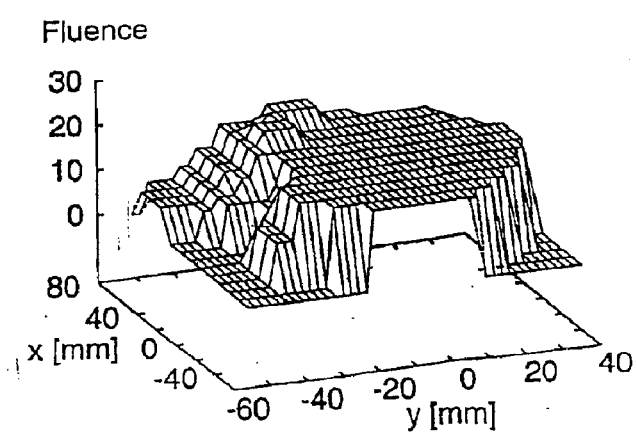
FIG. 5 shows the same field as FIG. 5, MLC constraints applied. The field has five segments.

The example is a prostate case with overlapping PTV and rectum. The optimisation algorithm used biological constraints and a gradient technique, as per reference 5. The five fields were arranged in gantry angles of 0, 72, 144, 216 and 288 degrees. The resolution of the fluence distribution was 10×2 mm² at the isocentre distance. The optimum treatment plan was computed without MLC constraints in about 10 minutes on a Pentium II/400 MHz and yielded an equivalent homogeneous dose to the PTV of 76.85 Gy. With inclusion of the translation operator, the fluence increment threshold was set to 5 MU which appears to be the lowest practical amount. The optimisation took 18 minutes and yielded a dose to the PTV of 76.55 Gy with a total of 39 segments. This marks a loss in target dose of less than 0.3 per cent. The target dose was subject to a homogeneity constraint so that we may conclude that the MLC constraint made the dose distribution less homogeneous, as can be seen from FIG. 3.

Of the five fields, two were unimodal and the remaining bimodal. The field from anterior oblique (72°) has five segments which can be applied with a minimum of leaf travel.

The field from posterior oblique (216°) has eight segments which can be separated into two leaf sweeps. As a consequence, a dynamic close-in technique would be advantageous for this case.

The number of segments is strongly dependent on the fluence increment threshold. If it is set to 10 MU, the same plan requires 27 segments at a loss of 0.5 per cent target dose. The number of segments could be reduced further if the beams were slightly rearranged such that the projection of the rectum aligns with the outline of the PTV. This measure would prove far more efficient than increasing the fluence increment threshold further.

Conclusion

The use of projection operators in iterative gradient based optimisation algorithms to ensure technical feasibility of the fluence profiles may lead to erratic behaviour and slow convergence. The strategy introduced here is to condition the fluence distribution such that the translation operator cannot disturb the convergence to an optimum and feasible solution. The method converges rapidly and allows to control the number of segments. For some treatment cases the number of segments may be as low as 20 without loss in the quality of the dose distribution. With few and relatively large field segments, IMRT becomes a viable alternative to standard treatment techniques.

References

1 M. Alber and F Nüsslin, "Intensity modulated photon beams subject to a miminal surface smoothness constraint" *Phys Med Biol*, 45:N49–N52, 2000

2 S. Webb, D. J. Convery and P. M. Evans, "Inverse planning with constraints to generate smoothed intensity-modulated beams", *Phys Med Biol.*, 43:2785–2794, 1998

3 M- A. Keller-Reichenbecher, T. Bortfeld, S. Levegrün, J. Stein, K. Preiser and W. Schlegel, "Intensity modulation with the 'step and shoot' technique using a commercial mic: a planning study", *Int. J. Rad. Oncol. Biol. Phys.*, 45:1315–1324, 1999

4 P. S. Cho and R. J. Marks, "Hardware-sensitive optimisation for intensity modulated radiotherapy", *Phys. Med. Biol.*, 45:429–440, 2000

5 M. Alber, M. Birkner, W. Laub and F. Nüsslin, "Constrained biological optimisation of imrt", submitted to *Phys. Med. Biol.*, 2000

What is claimed is:

1. An optimization method for a fluence pattern provided by a radiotherapeutic apparatus which includes a multi-leaf collimator, the method comprising:
   a progressive iterative solution of the fluence profile, in which:
   at least one earlier iteration includes a weighted penalty function that varies between:
   i. solutions favored by collimator design, and
   ii. solutions not favored by collimator design; and
   at least one later iteration includes the penalty function at a greater weight than the weight for the earlier iteration.

2. A method according to claim 1, in which the penalty function has multiple minima.

3. A method according torn claim 1, in which the penalty function represents locally preferred solutions derived from constraints of the multi-leaf collimator.

4. A method according to claim 3, in which the penalty function has multiple minima.

5. A method according to any of claims 1 to 4 in which the progressive iterative solution is a gradient based solution.

6. A method according to any of claims 1 to 4 in which the progressive iterative solution comprises:
   ascertaining a local gradient of a multi-dimensional surface representing the function to be minimized, and
   making a further iterative step in a direction corresponding to a downward gradient.

7. A method according to any of claims 1 to 4, in which the penalty function is calculated over a part of the fluence profile in a region of a present location of the iterating solution.

8. A method according to claim 7, in which the calculated part of the penalty function is centered at the present location of the iterating solution.

9. A method according to any of claims 1 to 4, in which the penalty function is re-calculated during each iteration.

10. A method according to claim 9 in which the recalculation involves adjustment of a location of the minima of the penalty function.

11. A computer program adapted to carry out a method according to claim 1.

12. A data carrier encoding a program according to claim 11.

13. A computing apparatus comprising a storage means in which a program is located and a processing means for running the program, the program being according to claim 11.

14. Radiotherapeutic apparatus comprising a source of radiation and a controller therefore, the controller being adapted to receive instructions from a computing apparatus according to claim 13.

* * * * *